United States Patent [19]

Bundy

[11] 3,996,266
[45] Dec. 7, 1976

[54] 4-OXA PHENYL-SUBSTITUTED PGE COMPOUNDS

[75] Inventor: Gordon L. Bundy, Portage, Mich.

[73] Assignee: The Upjohn Company, Kalamazoo, Mich.

[22] Filed: Oct. 23, 1975

[21] Appl. No.: 625,243

Related U.S. Application Data

[60] Division of Ser. No. 459,759, April 11, 1974, Pat. No. 3,931,289, which is a continuation of Ser. No. 185,448, Sept. 30, 1971, which is a continuation-in-part of Ser. No. 103,338, Dec. 31, 1970, abandoned.

[52] U.S. Cl. .................. 260/473 A; 260/345.7; 260/245.8; 260/520 B
[51] Int. Cl.² .................. C07C 5/22; C07C 9/76
[58] Field of Search ........ 260/473 A, 52 DB, 345.8

[56] References Cited

UNITED STATES PATENTS

| | | | |
|---|---|---|---|
| 3,864,387 | 2/1975 | Nelson | 260/473 A |
| 3,879,438 | 4/1975 | Crabbe et al. | 260/468 D |

*Primary Examiner*—Paul J. Killos
*Attorney, Agent, or Firm*—Morris L. Nielsen

[57] ABSTRACT

This invention is a group of 3-oxa and 4-oxa phenyl-substituted PGE type, PGF type, PGA type and PGB type compounds, and processes for making those. These compounds are useful for a variety of pharmacological purposes, including anti-ulcer, inhibition of platelet aggregation, increase of nasal patency, labor inducement at term, and wound healing.

28 Claims, No Drawings

4-OXA PHENYL-SUBSTITUTED PGE COMPOUNDS

CROSS REFERENCE TO RELATED APPLICATIONS

This is a division of application Ser. No. 459,759, filed Apr. 11, 1974 now U.S. Pat. No. 3,931,289, which is a continuation of my copending application Ser. No. 185,448, filed Sept. 30, 1971, which was a continuation-in-part of my copending application Ser. No. 103,338 filed Dec. 31, 1970, and now abandoned.

DESCRIPTION OF THE INVENTION

This invention relates to novel compositions of matter, to novel methods for producing them, and to novel chemical intermediates useful in those processes. Particularly, this invention relates to certain novel analogs of prostaglandins $E_1$, $E_2$, $F_{1\alpha}$, $F_1\beta$, $F_{2\alpha}$, $F_2\beta$, $A_1$, $A_2$, $B_1$, $B_2$, and the dihydro derivatives of the $PG_1$ compounds. These novel analogs each have an oxa oxygen (—O—) in place of the methylene (—$CH_2$—) moiety at the 3-position or at the 4-position of the prostanoic acid structure and also have a benzene ring as part of the C-13 to C-20 chain of the prostanoic acid.

The essential material for this application, including the background of the invention, the disclosure of the invention, and the description of the preferred embodiments, including Preparations and Examples, is incorporated by reference from U.S. Pat. No. 3,931,289, columns 1–101, inclusive, under the provisions of M. P. E. P. 608.01(p).

The following formulas represent the novel 4-oxa phenyl-substituted prostaglandin analogs of this invention:

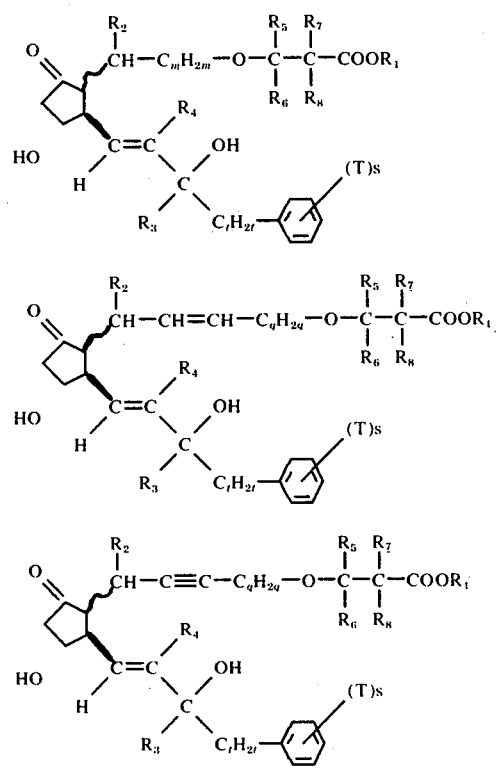

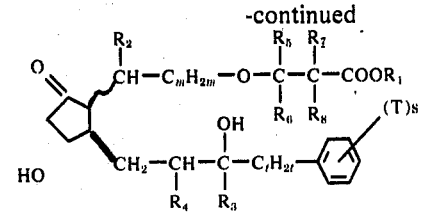

Formulas XII, XIV, XVI, and XVIII represent 4-oxa phenyl-substituted compounds of the PGE type.

In those formulas, $R_1$ is hydrogen, alkyl of one to 8 carbon atoms, inclusive, cycloalkyl of 3 to 10 carbon atoms, inclusive, aralkyl of 7 to 12 carbon atoms, inclusive, phenyl, phenyl substituted with one to 3 chloro or alkyl of one to 4 carbon atoms, inclusive, or ethyl substituted in the β-position with 3 chloro, 2 or 3 bromo, or 1, 2, or 3 iodo. $R_2$, $R_3$, $R_4$, $R_5$, $R_6$, $R_7$, and $R_8$ are hydrogen or alkyl of one to 4 carbon atoms, inclusive. The divalent moiety —$C_nH_{2n}$— represents alkylene of one to 10 carbon atoms, inclusive, with one to 5 carbon atoms, inclusive, between —$CHR_2$— and —O—. The divalent moiety —$C_mH_{2m}$— represents alkylene of one to 9 carbon atoms, inclusive, with one to 4 carbon atoms, inclusive, between —$CHR_2$— and —O—. The divalent moiety —$C_pH_{2p}$— represents alkylene of one to 8 carbon atoms, inclusive, with one, 2, or 3 carbon atoms between —CH=CH— or —C ≡ C— and —O—. The divalent moiety —$C_qH_{2q}$— represents alkylene of one to 7 carbon atoms, inclusive, with 1 or 2 carbon atoms between —CH=CH— or —C ≡ C— and —O—. The moiety —$C_tH_{2t}$— represents a valence bond, i.e., wherein $t$ is zero, or alkylene of one to 10 carbon atoms, inclusive, i.e., wherein $t$ is one to 10, substituted with zero, one, or 2 fluoro, with one to 7 carbon atoms, inclusive, between —$CR_3OH$— and the ring. When one or 2 fluoro are present as substituents of —$C_tH_{2t}$—, that moiety will contain $2t-1$ or $2t-2$ hydrogen atoms, respectively, rather than $2t$ hydrogen atoms. The symbol T represents alkyl of one to 4 carbon atoms, inclusive, fluoro, chloro, trifluoromethyl, or —$OR_9$, wherein $R_9$ is hydrogen, alkyl of one to 4 carbon atoms inclusive, or tetrahydropyranyl. The symbol $s$ represents zero, one, 2 or 3. Regarding the combination $(T)_s$ attached to the phenyl ring, no more than two T are other than alkyl. Except for that proviso, when two or three T are present as substituents, they are the same or different.

The wavy line ∼ in formulas XII, XIV, XVI, and XVIII indicates attachment of the group to the ring in alpha or beta configuration.

Formulas XII, XIV, XVI, and XVIII include lower alkanoates, and also pharmacologically acceptable salts when $R_1$ is hydrogen.

Also included in Formulas XII, XIV, XVI, and XVIII are separate isomers wherein the side chain hydroxy is in S or R (epi) configuration.

Included in Formula XIV, are both the cis and trans compounds with respect to the carbon-carbon double bond in the carboxy-terminated side chain. In all of the compounds containing —CH=$CR_4$—, that carbon-carbon double bond is in trans configuration, and the chain containing $R_4$ is attached to the cyclopentane ring in beta configuration in compounds encompassed by Formulas XII, XIV, XVI, and XVIII.

The novel 4-oxa phenyl-substituted prostaglandin analogs of this invention include racemic compounds and both optically active enantiomeric forms thereof.

As discussed hereinabove, two structural formulas are required to define accurately these racemic compounds. For convenience, only a single structural formula is used, for example, Formulas XII, XIV, XVI, and XVIII, to define the racemic form and both enantiomeric forms of each group of novel prostaglandin analogs. Each formula is, however, to be construed as including said racemic forms and both of said optically active enantiomeric forms.

I claim:
1. A compound of the formula:

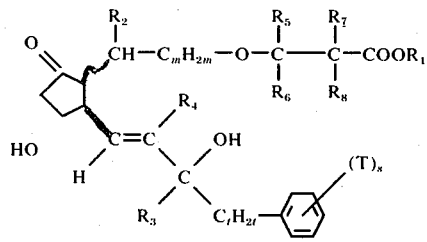

wherein $R_1$ is hydrogen, alkyl of one to 8 carbon atoms, inclusive, cycloalkyl of 3 to 10 carbon atoms, inclusive, aralkyl of 7 to 12 carbon atoms, inclusive, phenyl, phenyl substituted with one, 2 or 3 chloro or alkyl of one to 4 carbon atoms, inclusive, or ethyl substituted in the β-position with 3 chloro, 2 or 3 bromo, or 1, 2, or 3 iodo; wherein $R_2$, $R_3$, $R_4$, $R_5$, $R_6$, $R_7$, and $R_8$ are hydrogen or alkyl of one to 4 carbon atoms, inclusive; wherein $C_mH_{2m}$ is alkylene of one to 9 carbon atoms, inclusive, with one to 4 carbon atoms, inclusive, between —$CHR_2$— and —O—; wherein $C_tH_{2t}$ represents (1) a valence bond or (2) alkylene of one to 10 carbon atoms, inclusive, substituted with zero, one, or 2 fluoro, with one to 7 carbon atoms, inclusive, between —$CR_3OH$— and the ring; wherein T is alkyl of one to 4 carbon atoms, inclusive, fluoro, chloro, trifluoromethyl, or —$OR_9$, wherein $R_9$ is hydrogen, alkyl of one to 4 carbon atoms, inclusive, or tetrahydropyranyl, and s is zero, one, 2, or 3, with the proviso that no more than two T are other than alkyl; and wherein ~ indicates attachment of the group to the ring in alpha or beta configuration; including the lower alkanoates thereof, and the pharmacologically acceptable salts thereof when $R_1$ is hydrogen.

2. A compound according to claim 1 wherein

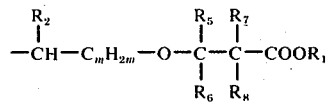

is

—$(CH_2)_3$—O—$(CH_2)_2COOR_1$ wherein $R_1$ is as defined in claim 1.

3. A compound according to claim 2 wherein $C_tH_{2t}$ is straight chain alkylene of one to 4 carbon atoms with or without a fluoro or alkyl substituent on the carbon atom adjacent to the hydroxy-substituted carbon atom.

4. A compound according to claim 3 wherein the side chain hydroxy is in S configuration.

5. A compound according to claim 4 wherein $R_4$ is hydrogen.

6. A compound according to claim 5 wherein $R_3$ is hydrogen.

7. A compound according to claim 6 wherein $C_tH_{2t}$ is $(CH_2)_d$ wherein d is one, 2, 3, or 4.

8. A compound according to claim 7 wherein d is 2.

9. 4-Oxa-17-phenyl-18,19,20-trinor-$PGE_1$, a compound according to claim 8.

10. 4-Oxa-17-phenyl-18,19,20-trinor-$PGE_1$, ethyl ester, a compound according to claim 8.

11. A compound according to claim 5 wherein $R_3$ is methyl.

12. A compound according to claim 11 wherein $C_tH_{2t}$ is $(CH_2)_d$ wherein d is one, 2, 3, or 4.

13. A compound according to claim 12 wherein d is 2.

14. 4-Oxa-15-methyl-17-phenyl-18,19,20-trinor-$PGE_1$, a compound according to claim 13.

15. 4-Oxa-15-methyl-17-phenyl-18,19,20-trinor-$PGE_1$, ethyl ester, a compound according to claim 13.

16. A compound according to claim 3 wherein the side chain hydroxy is in R (epi) configuration.

17. A compound according to claim 16 wherein $R_4$ is hydrogen.

18. A compound according to claim 17 wherein $R_3$ is methyl.

19. A compound according to claim 18 wherein $C_tH_{2t}$ is $(CH_2)_d$ wherein d is one, 2, 3, or 4.

20. A compound according to claim 19 wherein d is 2.

21. 15-Epi-4-oxa-15-methyl-17-phenyl-18,19,20-trinor-$PGE_1$, a compound according to claim 20.

22. 15-Epi-4-oxa-15-methyl-17-phenyl-18,19,20-trinor-$PGE_1$, ethyl ester, a compound according to claim 20.

23. A compound of the formula:

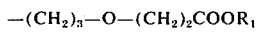

wherein $R_1$ is hydrogen, alkyl of one to 8 carbon atoms, inclusive, cycloalkyl of 3 to 10 carbon atoms, inclusive, aralkyl of 7 to 12 carbon atoms, inclusive, phenyl, phenyl substituted with one, 2, or 3 chloro or alkyl of one to 4 carbon atoms, inclusive, or ethyl substituted in the β-position with 3 chloro, 2 or 3 bromo, or 1, 2, or 3 iodo; wherein $R_2$, $R_3$, $R_4$, $R_5$, $R_6$, $R_7$, and $R_8$ are hydrogen or alkyl of one to 4 carbon atoms, inclusive; wherein $C_qH_{2q}$ is alkylene of one to 7 carbon atoms, inclusive, with one or 2 carbon atoms between —CH=CH— and —O—; wherein $C_tH_{2t}$ represents (1) a valence bond or (2) alkylene of one to 10 carbon atoms, inclusive, substituted with zero, one, or 2 fluoro, with one to 7 carbon atoms, inclusive, between —$CR_3OH$— and the ring; wherein T is alkyl of one to 4 carbon atoms, inclusive, fluoro, chloro, trifluoromethyl, or —$OR_9$, wherein $R_9$ is hydrogen, alkyl of one to 4 carbon atoms, inclusive, or tetrahydropyranyl, and s is zero, one, 2, or 3, with the proviso that no more than two T are other than alkyl; and wherein ~ indicates attachment of the group to the ring in alpha or beta configuration; including the lower alkanoates thereof, and the pharmacologically acceptable salts thereof when $R_1$ is hydrogen.

24. A compound according to claim 23 wherein

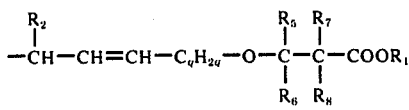

is

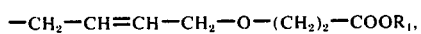

is

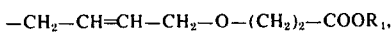

wherein $R_1$ is as defined in claim 23.

25. A compound of the formula:

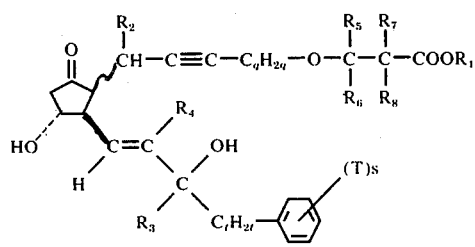

wherein $R_1$ is hydrogen, alkyl of one to 8 carbon atoms, inclusive, cycloalkyl of 3 to 10 carbon atoms, inclusive, aralkyl of 7 to 12 carbon atoms, inclusive, phenyl, phenyl substituted with one, 2, or 3 chloro or alkyl of one to 4 carbon atoms, inclusive, or ethyl substituted in the β-position with 3 chloro, 2 or 3 bromo, or 1, 2, or 3 iodo; wherein $R_2$, $R_3$, $R_4$, $R_5$, $R_6$, $R_7$, and $R_8$ are hydrogen or alkyl of one to 4 carbon atoms, inclusive; wherein $C_qH_{2q}$ is alkylene of one to 7 carbon atoms, inclusive, with one or 2 carbon atoms between —C≡C— and —O—; wherein $C_tH_{2t}$ represents (1) a valence bond or (2) alkylene of one to 10 carbon atoms, inclusive, substituted with zero, one, or 2 fluoro, with one to 7 carbon atoms, inclusive, between —CR$_3$OH— and the ring; wherein T is alkyl of one to 4 carbon atoms, inclusive, fluoro, chloro, trifluoromethyl, or —OR$_9$, wherein $R_9$ is hydrogen, alkyl of one to 4 carbon atoms, inclusive, or tetrahydropyranyl, and s is zero, one, 2, or 3, with the proviso that no more than two T are other than alkyl; and wherein ~ indicates attachment of the group to the ring in alpha or beta configuration; including the lower alkanoates thereof, and the pharmacologically acceptable salts thereof when $R_1$ is hydrogen.

26. A compound according to claim 25 wherein

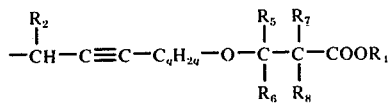

is

—CH$_2$—C≡C—CH$_2$—O—(CH$_2$)$_2$—COOR$_1$ is

—CH$_2$—C≡C—CH$_2$—O—(CH$_2$)$_2$—COOR$_1$ wherein $R_1$ is as defined in claim 25.

27. A compound of the formula:

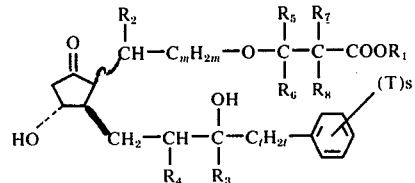

wherein $R_1$ is hydrogen, alkyl of one to 8 carbon atoms, inclusive, cycloalkyl of 3 to 10 carbon atoms, inclusive, aralkyl of 7 to 12 carbon atoms, inclusive, phenyl, phenyl substituted with one, 2, or 3 chloro or alkyl of one to 4 carbon atoms, inclusive, or ethyl substituted in the β-position with 3 chloro, 2 or 3 bromo, or 1, 2, or 3 iodo; wherein $R_2$, $R_3$, $R_4$, $R_5$, $R_6$, $R_7$, and $R_8$ are hydrogen or alkyl of one to 4 carbon atoms, inclusive; wherein $C_mH_{2m}$ is alkylene of one to 9 carbon atoms, inclusive, with one to 4 carbon atoms, inclusive, between —CHR$_2$— and —O—; wherein $C_tH_{2t}$ represents (1) a valence bond or (2) alkylene of one to 10 carbon atoms, inclusive, substituted with zero, one, or 2 fluoro, with one to 7 carbon atoms, inclusive, between —CR$_3$OH— and the ring; wherein T is alkyl of one to 4 carbon atoms, inclusive, fluoro, chloro, trifluoromethyl, or —OR$_9$, wherein $R_9$ is hydrogen, alkyl of one to 4 carbon atoms, inclusive, or tetrahydropyranyl, and s is zero, one, 2, or 3, with the proviso that no more than two T are other than alkyl; and wherein ~ indicates attachment of the group to the ring in alpha or beta configuration; including the lower alkanoates thereof, and the pharmacologically acceptable salts thereof when $R_1$ is hydrogen.

28. A compound according to claim 27 wherein

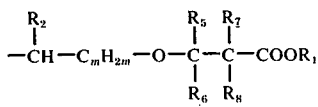

is

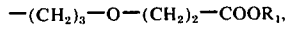

is

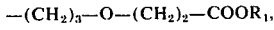

wherein $R_1$ is as defined in claim 27.

* * * * *

UNITED STATES PATENT OFFICE
CERTIFICATE OF CORRECTION

Patent No. 3,996,266  Dated December 7, 1976

Inventor(s) Gordon L. Bundy

It is certified that error appears in the above-identified patent and that said Letters Patent are hereby corrected as shown below:

Column 1, line 44 "  " should read --  --; line 54, "  " should read --  --; line 63, "  " should read -- 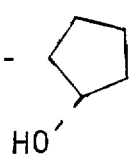 -- . Column 2, line 7, "  " should read --  --. Column 3, line 17, "  " should read --  --. Column 4, lines 54-5, "-CH=λCH-" should read -- CH=CH- --. Column 5, claim 24, lines 8-10, "-CH$_2$-CH=CH-CH$_2$-O-(CH$_2$)$_2$-COOR$_1$" appears twice. Column 6, lines 2-4, "is -CH$_2$-C≡C-CH$_2$-O-(CH$_2$)$_2$-COOR$_1$" appears twice; lines 50-52 "is -(CH$_2$)$_3$-O-(CH$_2$)$_2$-COOR$_1$" appears twice Signed and Sealed this Sixth Day of September 1977

[SEAL]

Attest:

RUTH C. MASON
Attesting Officer

LUTRELLE F. PARKER
Acting Commissioner of Patents and Trademarks